(12) United States Patent
Schwartz et al.

(10) Patent No.: US 10,342,410 B2
(45) Date of Patent: Jul. 9, 2019

(54) AUTOMATED SYSTEM FOR MEDICAL VIDEO RECORDING AND STORAGE

(71) Applicant: Virgo Surgical Video Solutions, Inc., San Francisco, CA (US)

(72) Inventors: Matthew Zane Schwartz, San Francisco, CA (US); Ian Christopher Strug, Chicago, IL (US); David Oscar Guaraglia, San Francisco, CA (US)

(73) Assignee: Virgo Surgical Video Solutions, Inc., San Francisco, CA (US)

( * ) Notice: Subject to any disclaimer, the term of this patent is extended or adjusted under 35 U.S.C. 154(b) by 16 days.

(21) Appl. No.: 15/793,502

(22) Filed: Oct. 25, 2017

(65) Prior Publication Data
US 2018/0110398 A1   Apr. 26, 2018

Related U.S. Application Data

(60) Provisional application No. 62/413,040, filed on Oct. 26, 2016.

(51) Int. Cl.
| | |
|---|---|
| *A61B 1/00* | (2006.01) |
| *G06K 9/00* | (2006.01) |
| *G16H 30/40* | (2018.01) |
| *G16H 30/20* | (2018.01) |
| *G16H 50/20* | (2018.01) |

(52) U.S. Cl.
CPC ........ *A61B 1/00006* (2013.01); *A61B 1/0002* (2013.01); *A61B 1/00009* (2013.01); *A61B 1/00016* (2013.01); *A61B 1/00039* (2013.01); *A61B 1/00055* (2013.01); *G06K 9/00496* (2013.01); *G16H 30/20* (2018.01); *G16H 30/40* (2018.01); *G16H 50/20* (2018.01)

(58) Field of Classification Search
CPC ............ A61B 1/00006; A61B 1/00009; A61B 1/00016; A61B 1/0002; A61B 1/00039; A61B 1/00055; G06K 9/00496; G16H 10/60
See application file for complete search history.

(56) References Cited

U.S. PATENT DOCUMENTS

| | | | |
|---|---|---|---|
| 2009/0189981 A1* | 7/2009 | Siann ...................... | H04N 7/183 348/143 |
| 2013/0107041 A1* | 5/2013 | Norem .................. | H04N 5/225 348/143 |

(Continued)

FOREIGN PATENT DOCUMENTS

JP         2010051399 A   *   3/2010

*Primary Examiner* — Huy T Nguyen

(57) ABSTRACT

A method and device for automatically recording a video output signal from an endoscopy device. Video image data is received at a video capture device, and transmitted with associated metadata to a server. Prior to transmission, the video capture device analyzes the video image data to identify a recording start indicator as a function of predetermined threshold conditions. Once the indicator is identified, the device sends recording start timestamp to a backend server. The server indexes and stores the recorded video data as a function of the associated metadata in a database, and also records the recording the recording start timestamp data in the database. The device is further able to identify a recording stop indicator, and prepare recording stop timestamp data for transmission to the server.

29 Claims, 10 Drawing Sheets

(56) References Cited

U.S. PATENT DOCUMENTS

2015/0208900 A1* 7/2015 Vidas ................. A61B 1/00009
348/74
2015/0313445 A1* 11/2015 Davidson .............. G06T 3/4038
600/109

* cited by examiner

900

Finish Procedure

Are you sure you want to finish
the current procedure? ← 901

[CONFIRM] ← 902

AUTOMATED SYSTEM FOR MEDICAL VIDEO RECORDING AND STORAGE

RELATED APPLICATION

This application claims the benefit of priority under 35 § 119(e) to U.S. Provisional Patent Application No. 62/413,040, entitled "An Automated System for Medical Video Recording and Storage," filed on Oct. 26, 2016 and incorporated by reference in its entirety herein.

FIELD OF THE INVENTION

This disclosure pertains to a system and method for recording and storing video images produced by a medical device, and more particularly, to a system and method for recording medical video images from an endoscopy device that automatically determines when to start and stop recording based on an analysis of the associated video images.

BACKGROUND

Medical video has become an integral part of various forms of healthcare delivery, for example including many diagnostic and surgical procedures. The settings in which these procedures are administered are often high-intensity environments, with significant attention paid to patient care by physicians and attending staff. As such, the associated medical providers have limited resources and attention to devote to optimizing their use of information technology. In particular, providers in many cases struggle to efficiently record and store medical video obtained during the procedures.

Medical video recording devices currently on the market typically require a significant amount of user interaction to begin and end recording, including for example user registration, file formatting, and storage formatting. The effort involved significantly limits actual usage of the medical recoding devices.

SUMMARY

By way of example, aspects of the present disclosure are directed to a system and method for automatically recording a video output signal during a recording session, for example from an endoscopy device during the administration of a medical procedure.

In accordance with aspects of the present disclosure, the method for automatically recording a video output signal from an endoscopy device during a recording session includes the steps of: a) receiving video image data of the video output signal at a video capture device, b) transmitting signals corresponding to the video image data and associated metadata to the server via the video capture device, c) analyzing the video image data by the video capture device to identify a recording start indicator for the recording session as a function of predetermined threshold conditions, d) setting a recording start timestamp by the video capture device, e) transmitting the recording start timestamp data over the network to the server via the video capture device, f) indexing the recorded video data by the server as a function of the associated metadata, g) storing the indexed video data for the recording session in a database accessible to the server; and h) storing the recording start timestamp for the recording session in the database.

In accordance with an additional aspect of the present disclosure, the video capture device includes a) at least one input port configured for receiving a video output signal from the an endoscopy device, b) a processor in communication with the at least one input port, c) a local storage device accessible by the first processor, and d) at least one output device in communication with the processor and configured for accessing a network, where the processor is operable to analyze video image data of the video output signal, identify a recording start indicator for the recording session as a function of predetermined threshold conditions for the video image data, and prepare and transmit recorded video data including the video image data to the network via the at least one output device upon identifying the recording start indicator. The predetermined threshold conditions for identifying a recording start indicator are selected to indicate when the endoscopy device is internally positioned within a patient body cavity, thereby eliminating external footage which could compromise privacy protections.

Further in accordance with another aspect of the present disclosure, the video capture device is operable to analyze the video image data to identify a recording stop indicator for the recording session as a function of the predetermined threshold conditions for the video image data, set a recording stop timestamp and transmit recording stop timestamp data for storage for the recording session in the database.

Preferably, the video capture device as presently disclosed in addition includes at least one input port configured for receiving an audio input signal from at least one microphone, and circuitry for transmitting the audio data, associated metadata and an associated timestamp for storage for the recording session in the database.

By automatically determining start and stop indicators for the recording session, the method and device reduce the need for user interaction to facilitate a recording session. By reducing the necessary level of interaction, it becomes more likely that video data produced during a medical procedure will be recorded. The system automatically determines the appropriate time to begin recording and storing a specific medical event video based on image analysis. This eliminates the need for healthcare provider staff to interact with a device in order to initiate and end video recording and storage. Once the video is recorded, it is stored in a manner such that it is secure and HIPAA-compliant.

This SUMMARY is provided to briefly identify some aspects of the present disclosure that are further described below in the DESCRIPTION. This SUMMARY is not intended to identify key or essential features of the present disclosure nor is it intended to limit the scope of any claims.

BRIEF DESCRIPTION OF THE DRAWING

A more complete understanding of the present disclosure may be realized by reference to the accompanying drawing in which:

FIG. 9 depicts a fifth screen image associated with a user portal of the system of FIG. 1.

DETAILED DESCRIPTION

The following merely illustrates the principles of the disclosure. It will thus be appreciated that those skilled in the art will be able to devise various arrangements which, although not explicitly described or shown herein, embody the principles of the disclosure and are included within its spirit and scope.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements later developed that perform the same function, regardless of structure.

Unless otherwise explicitly specified herein, the drawings are not drawn to scale.

Figure 1:
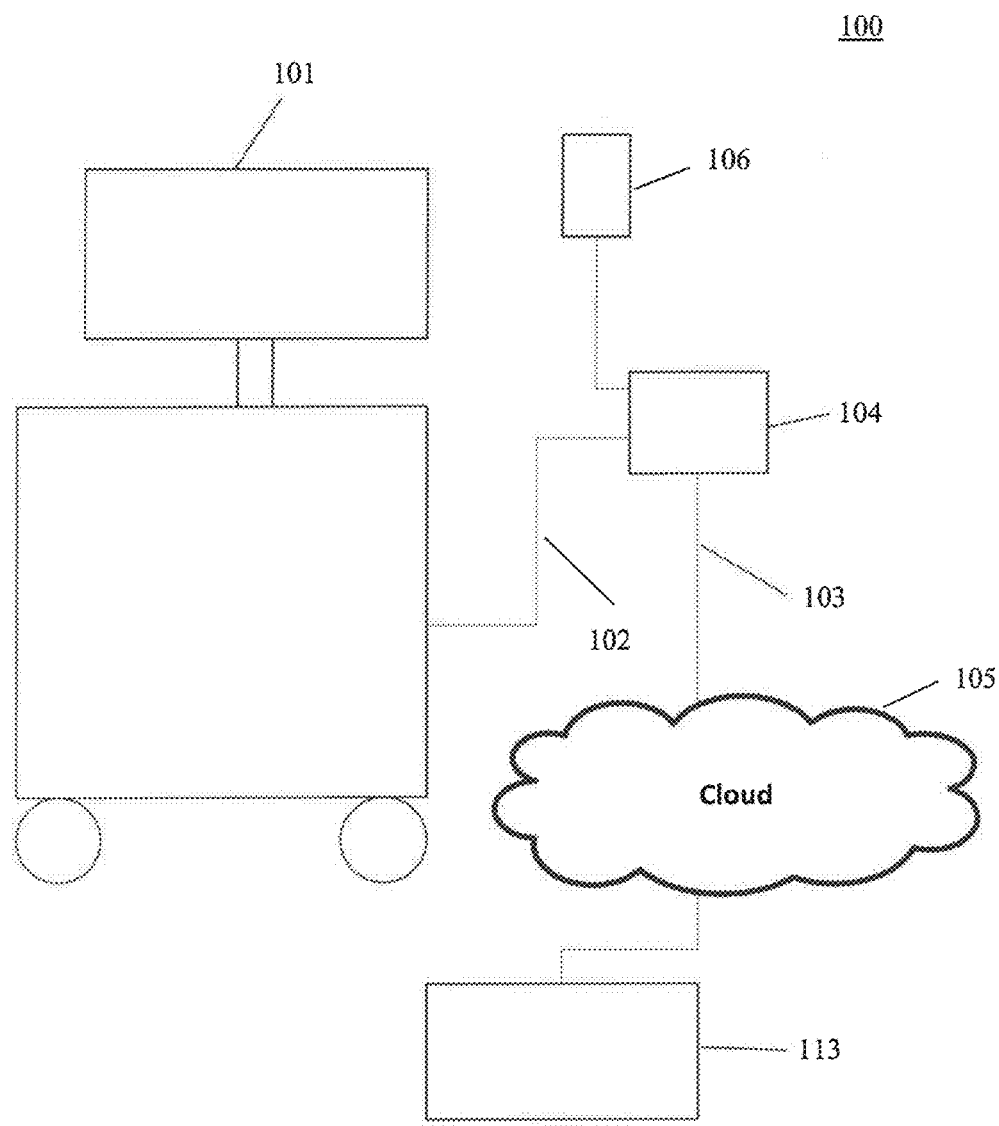
FIG. 1 presents a schematic diagram depicting a system for capturing and recording video output from an endoscopy procedure in accordance with aspects of the present disclosure.

FIG. 1 depicts a system 100 for capturing and recording video output from an endoscopy procedure in accordance with aspects of the present disclosure. A video capture system 104 of the system 100 receives a video image from a video input source 102 that originates from an endoscopic imaging system 101 for obtaining a video image from an endoscope positioned in an internal body cavity of a patient. The system 101 may comprise any of a number of commercially-available endoscopic imaging systems, for example including the PINPOINT endoscopic fluorescence imaging system available from NOVADAQ of Bonita Springs, Fla. Imaging may be directed to any of a variety of endoscopic devices, including but not limited to arthroscopes, cystoscopes, hysteroscopes, laparoscopes, laryngoscopes, endoscopes, resectoscopes, sinuscopes. uteroscopes and colonoscopes.

The video input source 102 may implemented using any of a variety of commercially-available video interface technologies, for example including a digital visual interface (DVI) video display interface. The video capture system 104 processes the video and provides a video output over a network connection 103. The network connection 103 may be implemented for example a wireless transmitter of the video capture system 104 that wirelessly communicates with a wireless local area network (WLAN) such as a Wi-Fi network, or non-wirelessly via an output port of the system 104 with an Ethernet LAN. Video output to the WLAN or Ethernet LAN may be transmitted over the Internet and/or other commercially-available networks to a commercially-available cloud-based storage service 105, for example such as AMAZON WEB SERVICES (AWS) cloud computing and storage services available from AMAZON.COM of Seattle, Wash.

Cloud-based storage service 105 is accessible by a back-end server 113 and associated software, which provides a secure user portal for operating the system 100, for example, via the Internet and/or other commercially-available networks. The portal may for example be accessed via a workstation of the endoscopic imaging system 101, or via a variety of mobile device and/or personal electronic devices including smartphones, tablet computers and the like.

Figure 2:
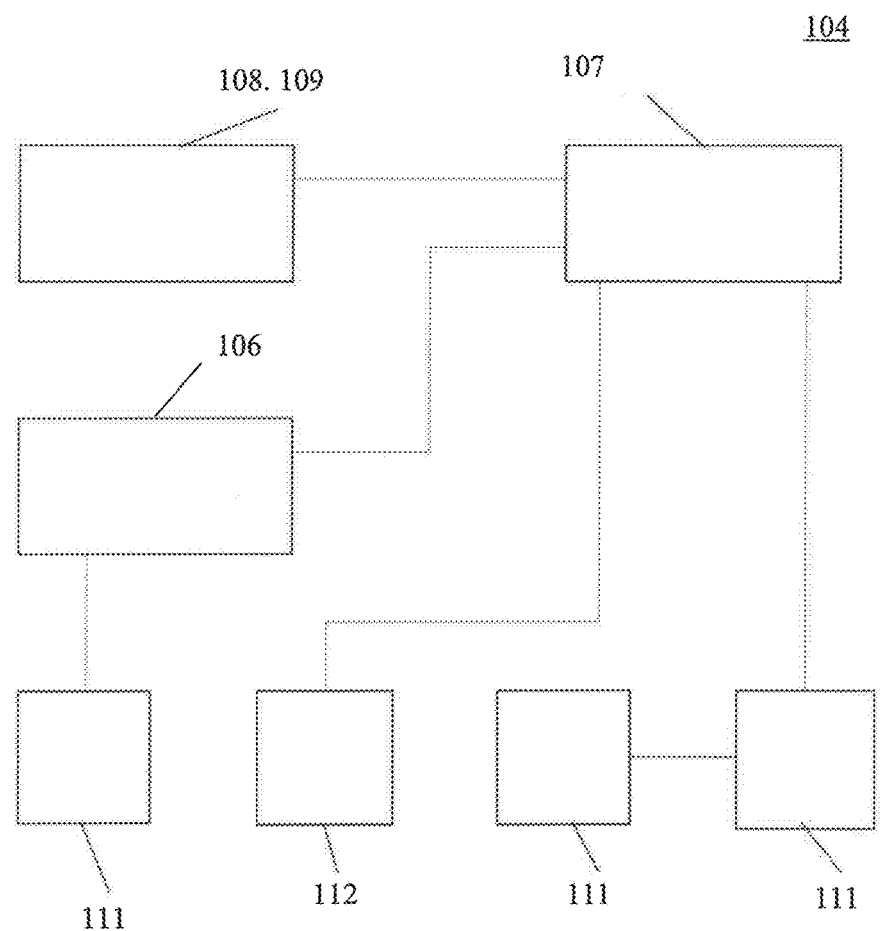
FIG. 2 presents a schematic diagram illustrating a video capture device of the system of FIG. 1.

FIG. 2 further illustrates the video capture device 104 of FIG. 1. The device 104 includes at least one commercially-available central processing unit (CPU) 107 that including specialized software and/or hardware implementing video processing and/or Wi-Fi functionality. Preferably, the at least one CPU 107 includes a CPU/graphics processing unit (GPU) processor pair for more efficient video processing. One suitable CPU/GPU pair may be provided in the RASPBERRY PI 3 available from the RASPBERRY PI FOUNDATION, Cambridge, UK, which includes a Broadcom BCM2836 CPU and Broadcom VideoCoreIV-AG100-R GPU supporting H.264 encoding. The video capture device 104 may also preferably include an on-board battery 106, either as an alternative or back-up to commercial power source provided via power input 111. In addition, the device 104 may include a memory 109, for example such as a micro SD card memory available from the SANDISK of Milpitas, Calif., storing the operation system (OS) for the CPU 107 and other applications. For example, the OS may be a resinOS from RESIN.IO of Seattle, Wash.

One or more video inputs 110 are preferably provided, for example providing a DVI to High-Definition Multimedia Interface (HDMI) interface for coupling with the CPU 107. The device 104 may also preferably include an Ethernet port 112 for coupling to a corresponding Ethernet port of the CPU 107. In addition, the device may include an audio input port, for example, implemented as a Universal Serial Bus (USB) port suitable for receiving a USB microphone, for example, such as a SAMSON Stage XPD1 BLUETOOTH digital wireless microphone available from Samson Technologies Corporation of Hicksville, N.Y. Alternatively, for example, audio inputs may be received via an integrated audio microphone device of the video capture device 104, or may be processed by a digital assistant device (for example, an ECHO device available from AMAZON.COM of Seattle, Wash.) in communication with the network connection 103.

Figure 3:
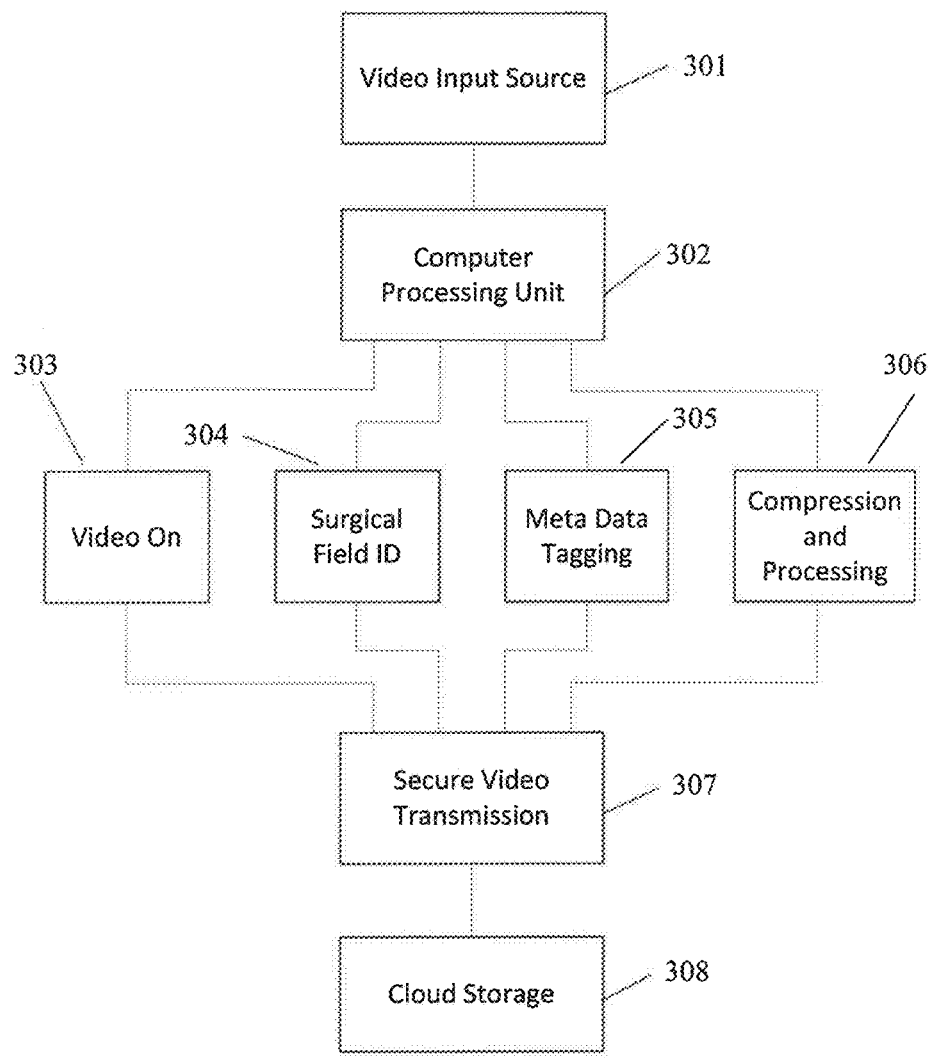
FIG. 3 presents a flow diagram illustrating a method of operation for the system of FIG. 1.

FIG. 3 illustrates a method of operation for the system 100 of FIG. 1. At step 301, a video image stream is transmitted via video input source 102 and received at step 302 by CPU/GPU 107. CPU/GPU 107 recognizes that video transmission is active at step 303, and then optionally determines whether recording should proceed at step 304 by analyzing the video image stream to determine whether the endoscope has entered a surgical field internal to the patient. Alternatively, the physician may manually signal for recording to proceed via the secure user portal provided via the backend server 113. At step 305, the CPU/GPU 107 packages portions of the video image stream ("blocks") for transmission, and applies meta data tagging to identify the blocks (for example, including recording session and block sequence identifiers). The size of the blocks may preferably be variably optimized for storage size and efficiency of transmission.

At step 306, the CPU/GPU 107 preferably applies compression and encryption processing (for example, H.264 compression and encryption processing), and then prepares the video stream blocks for transmission via network connection 103 at step 307. The transmitted video stream blocks are received and stored by cloud storage service 105 at step 308. Preferably, data is transferred by the device 104 to the cloud storage service 105 using a SFTP secure file transfer protocol, and maintained in an encrypted form both during transmission and in storage, using an encryption key management service such as AWS Key Management Service from AMAZON.COM of Seattle, Wash.

Figure 4:
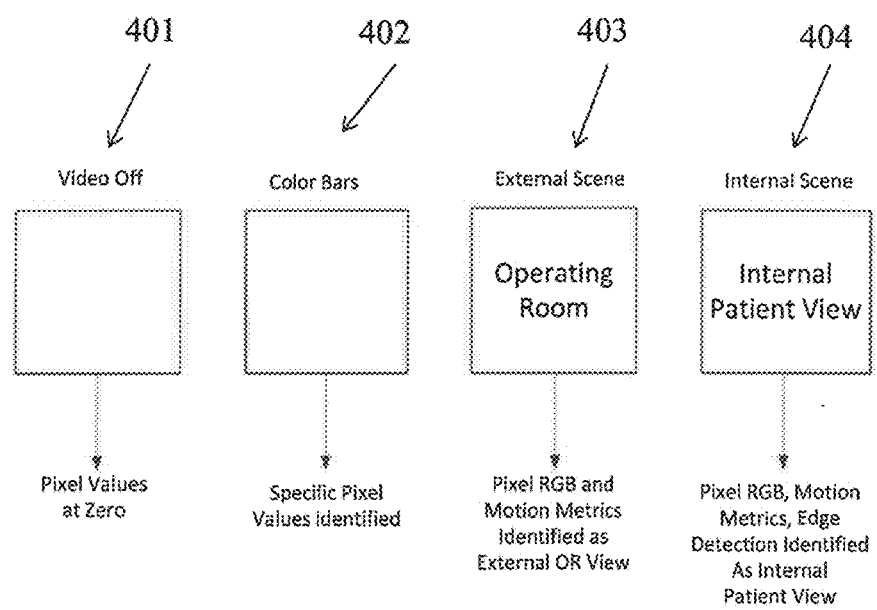
FIG. 4 illustrates an analysis sequence in accordance with aspects of the present disclosure for determining whether an endoscope recorded by the video recording system of FIG. 1 is positioned internally or externally with respect to a patient.

In further explanation of step 304 of FIG. 3, and by way of example, FIG. 4 illustrates an analysis sequence for automatically determining whether video stream recording should begin and/or end. In order to facilitate privacy protections, the analysis is directed to limit recording to the video stream by the endoscope while positioned in an internal body cavity of the patient. In other words, no recording should occur when the endoscope is positioned outside a body cavity and thereby is capable, for example, to record identifying images of the patient and/or medical staff.

CPU/GPU 107 preferably runs imaging and video analysis algorithms on a continuous bases to properly determine when the appropriate video footage is being input to start recording. These algorithms may, for example, be directed to analyze pixel color (RGB) values, frame-to-frame motion shifts, and edge or contour detection to determine the appropriateness of the incoming footage. When the proper video input is detected it will trigger the system to start recording. This video data will then be recorded and securely transmitted in digestible blocks for storage by the cloud storage service 105. Software associated with the backend server 113 will properly reassemble the digestible data blocks into a single file, assign the correct metadata, and store the files with the cloud storage service 105.

FIG. 4 illustrates several example stages of analysis. At stage 401, the CPU/GPU 107 determines by analyzing pixel color values that no video image signal is being provided. At stage 402, the CPU/GPU 107 registers specific pixel color values for the video image stream and determine that the video image signal is "on." At stage 403, as a result for example of analyzing RGB values and frame-to-frame motion shifts, the CPU/GPU 107 determines that the video image is associated with details of the medical procedure or operating room, and that recording therefor should be "off." At stage 404, as a result for example of analyzing RGB values, frame-to-frame motion shifts and edge detection, the CPU/GPU 107 determines that video image is associated with a body cavity internal to the patient, and that recording should be "on" and proceed.

It should be noted that the specific RGB values, frame-to-frame motion shift and edge detection algorithms use will be adjusted depending on their application. For example, algorithms to detect laparoscopic surgical footage may differ slightly from algorithms to detect colonoscopy diagnostic footage. In this regard, it may be preferable to provide a mechanism for training the CPU/GPU 107 to recognize specific applications, for example, by including and/or providing access to a neural network for this purpose (for example, incorporating at least one of a convolutional neural network or a recurrent neural network).

Such neural networks may be optimally trained for various applications (for example, laparoscopic procedures versus colonoscopies). In many cases, such neural networks will be best equipped for handling variance in the incoming data streams (for example, changes in white balance or resolution) due to their ability to generalize to new data. In addition to these algorithms, there may be proper time, date, room and patient ID logic gates to trigger starting and stop of the recordings.

In addition to determining starting and stop points of the recording automatically, it may be advantageous to also provide the physician and/or support staff with a direct way to indicate starting and stop points. For example, and as illustrated with reference to FIGS. 8 and 9, physicians and support staff may be provided with a mechanism to manually start and stop recording via a user portal provide by the backend server 113 of FIG. 1, using for example a conventional keyboard, mouse or other user interface control (for example, a foot pedal).

As another alternative, the audio input port described with reference to the video capture device 104 of FIG. 2 may provide a mechanism for physicians and/or support staff to provide starting and stop indicators by means of oral commands enunciated via a microphone in communication with the audio input port (for example, enunciated as "Virgo start" or "Virgo stop"). In addition, a command may be made available for recording physician notes in real time in reference to a procedure (for example, the physician signals the introduction of a note by enunciating "Virgo take note," and then orally provides the note—for example. "I see a serrated sessile polyp in the upper right quadrant of the screen, approximately 5 mm in diameter").

Preferably, in accordance with aspects of the present disclosure, starting and stop points in the video image recording for a recording session are managed by means of associated timestamps generated by the video capture device 104 and transmitted for storage by the cloud storage service 105 of FIG. 1. For example, for a playback session managed via backend server 113 (and identified, for example, by associated metadata including one or more of a date, time, location and/or patient/physician identifier), a recording start timestamp may be retrieved and used initiate playback by selecting a first stored video image data segment having time data included in associated metadata that matches the recording start timestamp. Similarly, a recording stop timestamp may be used to identify a last stored video image data segment that concludes the playback session. The associated metadata for the first, last and intervening video image data segments may preferably include sequence identifiers used during storage and/or playback to sequence the video image data segments for playback. Alternatively, the system may pair recording start and stop timestamps by source (for example, by automated vide analysis or audio command), and record and store separate video sequences ("clips") corresponding to each timestamp pair.

The other alternative mechanisms for signaling starting and stop points (for example, including the user portal and audio input described above) may also preferably be configured to generate timestamps for storage by the cloud storage service 105. Backend server 113 is preferably provided with access to a series of rules to resolve any apparent conflicts that may be generated by storing multiple recording start and stop timestamps for an individual recording session (as could be generated by execution of these several alternative means). In view of privacy concerns, for example, one rule set might resolve conflicts by selecting a latest one of the recording start timestamps and an earliest one of the recording stop timestamps to set the boundaries of the recording playback session.

Although described herein with reference to FIG. 1 as a system comprising the video capture device 104, cloud storage service 105 and backend server 113, one of ordinary skill in the art will recognize for example that the various components and functions provided by each one of these elements could be performed by another one of these elements, or by collection of these and/or other elements having network connectivity (for example, as a so-called "internet of things" system distributed within a medical facility, with an on-site interface device communicating with backend server 113). Similarly, the backend system described as backend server 113 could alternatively be configured among a variety of distributed elements.

A person using this system to record and store medical video may preferably operate the video capture device in a mode that is permanently on and connected to a medical video source. In this mode, the CPU 107 of the device 104 can continuously run the imaging and video analysis algorithms in the background to automatically determine when to start and stop recording. In this manner, minimal user interaction will be needed once the system is setup. The system may also preferably monitor its own functionality, assisted by associated telemetry monitoring in the medical facility and the backend server. Such telemetry may for example preferably include monitoring of power consumption, internet network capacity, temperature of the system and aspects of the video connection.

Physician or technician operation of the video capture and recording system 100 may be facilitated by means of a user's portal, preferably implemented as a software service on backend server 113. Some aspects of the portal as described below may alternatively be implemented in other devices, for example including the video capture device 104.

FIGS. 5-10 provide example screens in a user interface of the portal, as presented on a workstation that may preferably be located in a medical procedure or operating room within which the endoscopic imaging system 101 may reside. The user interface of the portal may alternatively be implemented for display on a variety of other devices, for example including smartphones, tablets and other personal mobile devices.

Figure 5:
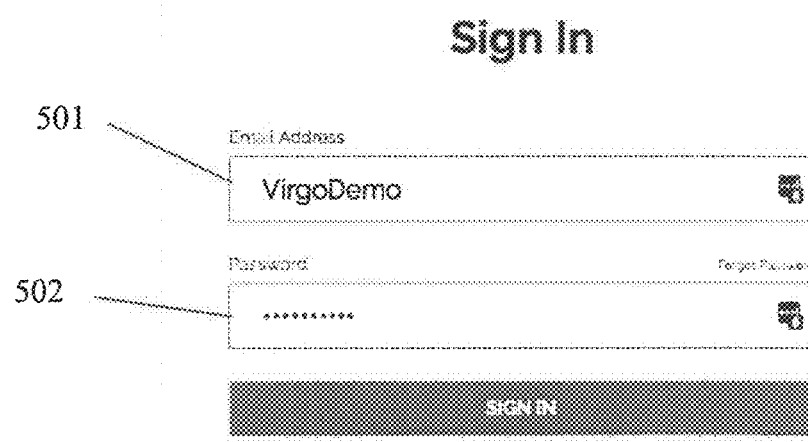
FIG. 5 depicts a first screen image associated with a user portal of the system of FIG. 1.

FIG. 5 illustrates an exemplary sign-in screen 500 that may presented to a user for obtaining secured access to the user portal via the workstation. The sign in screen 500 may preferably require the user to present login and password credentials in order to secure access to information associated with a user account.

Figure 6:
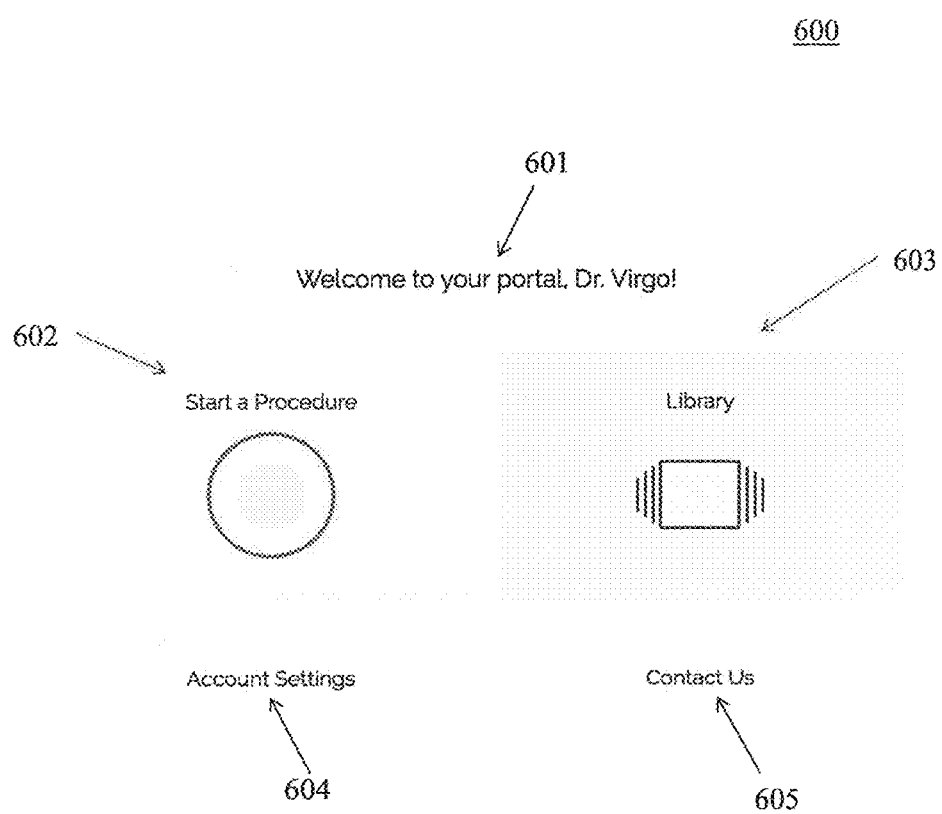
FIG. 6 depicts a second screen image associated with a user portal of the system of FIG. 1.

FIG. 6 illustrates an exemplary menu page 600 that may be presented to a user after obtaining access to the portal via the sign-in screen 500. The menu page 600 may preferably present a welcome banner 601 that identifies the user in order to confirm that an appropriate sign-in procedure was achieved. The menu may further present an executable icon 602 for initiating a video image recording session, an executable icon 603 for accessing a library of video images previously recorded by the user, an executable icon 604 for managing the user's account (for example, setting preferences for automatic and manual recording), and an executable icon 605 for obtaining assistance.

Figure 7:
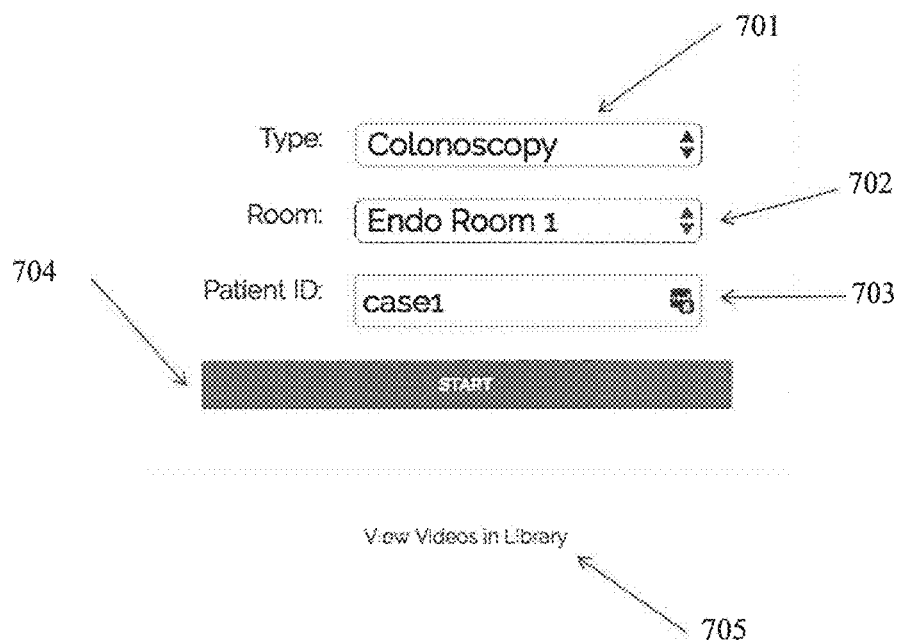
FIG. 7 depicts a third screen image associated with a user portal of the system of FIG. 1.

FIG. 7 illustrates an exemplary start page 700 for initiating a video image recording procedure. By means for example of a drop-down menu, the user selects a procedure type 701 ("Colonoscopy"), specifies a procedure location 702 ("Endo Room 1"), and provides a patient or case identifier 703 ("case 1"). When complete, the user selects a start button 704 which may, for example, result with the presentation to the user of the recording start page 800 depicted in FIG. 8. On the recording start page 800, the user is able to check and verify associated procedure information 801 identifying procedure type, procedure location and patient or case identifier information entered on the start page 700 of FIG. 7. In addition, the backend server 113 may for example add date and time information. With referenced to FIG. 3, some or all of the associated procedure information 801 may be used to prepare metadata for the metadata tagging step of FIG. 3.

Figure 8:
FIG. 8 depicts a fourth screen image associated with a user portal of the system of FIG. 1.
Figure 8:
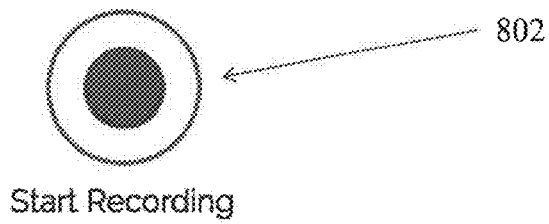
Figure 8:

Once the associated procedure information 801 has been confirmed and the vision system of the endoscope has been positioned within a patient body cavity, the user may initiate recording by selecting the start recording button 802 illustrated in FIG. 8 (for example, by operation of a workstation mouse). Alternatively, the user may employ another input/output (I/O) device in communication with the workstation (for example, including foot pedals, a wireless control fob, or one of a variety of voice-actuated controls including digital assistants such as SIRI, ALEXA, CORTANA and/or other Open-Source alternatives). Alternatively and preferably, as discussed above for example with reference to FIG. 4, recording may be automatically initiated with the placement of the vision system of the endoscope in the patient body cavity by means of an analysis of the video image stream using algorithms directed to analyzing one or more of RGB values, frame-to-frame motion shifts, and edge and/or edge movement detection.

When the procedure has been completed, the user can terminate recording by selecting the finish procedure button 803 of FIG. 8. Alternatively, and similarly to what was described above with reference to the start recording button 802, recording may be stopped manually by the user by means of a variety of I/O devices other than a workstation mouse, or more preferably, automatically stopped by means of an analysis of the video image stream using algorithms directed to analyzing one or more of RGB values, frame-to-frame motion shifts, and edge and/or edge movement detection. Thereafter, the user may preferably be presented with a finish procedure confirmation page 900, which may present a confirmation message 901 ("Are you sure you want to finish the current procedure?") and confirm button 902 that can be selected to confirm that the procedure be finished. The confirmation page 900 may or may not be presented to the user in the case that it is automatically determined to finish the procedure by means of the algorithms directed to analyzing one or more of RGB values, frame-to-frame motion shifts, and edge and/or edge movement detection.

Figure 10:
FIG. 10 depicts sixth screen image associated with a user portal of the system of FIG. 1.
Figure 10:
Figure 10:
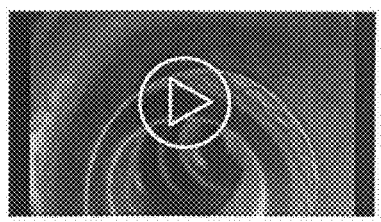

Returning to FIG. 7, before beginning a procedure, the user may wish to review video recordings from similar procedures as a guide. In this case, the user may select review button 705 ("View Videos in Library") and be directed for example to a video library page 1000 as illustrated in FIG. 10. Library page 1000 presents recording links 1001, 1002 to the user for playback. In accordance with a permissions protocol, the page 1000 preferably identifies only those recordings that a user is eligible to view. Associated video image data retrieved for playback in each case is limited to video data recorded between the associated start and stop timestamps.

REFERENCE CHARACTER TABLE

The following table lists the reference characters and names of features and elements used herein:

| | Feature or element |
|---|---|
| 100 | Video capture and recording system |

-continued

| | Feature or element |
|---|---|
| 101 | Endoscopic imaging system |
| 102 | Video input source |
| 103 | Network connection |
| 104 | Video capture device |
| 105 | Cloud storage service |
| 106 | Power source |
| 107 | CPU |
| 108 | Device Software |
| 109 | Device Digital Storage |
| 110 | Video Input |
| 111 | Power Input |
| 112 | Ethernet port |
| 113 | Backend Server |

It will be understood that, while various aspects of the present disclosure have been illustrated and described by way of example, the invention claimed herein is not limited thereto, but may be otherwise variously embodied within the scope of the following claims. For example, it should be understood that this invention could potentially be used in other fields to automatically record video in specific situations. The primary embodiment of this invention is applied to medical video, but other specific video sources could be applied as well. The invention can potentially produce additional useful information through the data that is collected. With sufficient quantities of recorded medical video data, the invention can provide insights, specifically with big data analysis techniques.

We claim:

1. A video capture device for automatically recording a video output signal from an endoscopy device during a recording session, comprising:
at least one input port configured for receiving the video output signal from the endoscopy device;
at least one processor in communication with the at least one input port,
a local storage device accessible by the first processor, and
at least one output device in communication with the processor and configured for accessing a network,
wherein the at least one processor is operable to analyze video image data of the video output signal, identify a recording start indicator for initiating the recording session as a function of predetermined threshold conditions for the video image data, and prepare and transmit recorded video data including the video image data to the network via the at least one output device upon identifying the recording start indicator,
wherein the predetermined threshold conditions are based on two or more elements selected from the group consisting of pixel values, frame-to-frame motion metrics, edge detection indicators, audio signals, neural networks, convolutional neural networks, and recurrent neural networks and
wherein the at least one processor identifies the recording start indicator to initiate the recording session only when the threshold conditions indicate that the medical device is displaying video image data internal to a patient.

2. The video capture device of claim 1, wherein the at least one processor comprises at least one central processing unit (CPU) and at least one graphics processing unit (CPU).

3. The video capture device of claim 1, wherein the endoscopy device is selected from the group consisting of arthroscopes, cystoscopes, hysteroscopes, laparoscopes, laryngoscopes, endoscopes, resectoscopes, sinuscopes, uteroscopes and colonoscopes.

4. The video capture device of claim 1, wherein the at least one processor is further operable to set a recording start timestamp and transmit the recording start timestamp to the network via the at least one output port.

5. The video capture device of claim 1, wherein the at least one processor is further operable to identify a recording stop indicator for the recording session as a function of the predetermined threshold conditions, set a recording stop timestamp and transmit the recording stop timestamp to the network via the at least one output port, and
wherein the at least one processor identifies the recording stop indicator to terminate the recording session when the threshold conditions indicate that the medical device is displaying video image data external to the patient.

6. The video capture device of claim 1, wherein the recorded video data further includes metadata associated with the video image data.

7. The video capture device of claim 6, wherein the associated metadata includes one or more elements selected from the group consisting of a calendar date, a timestamp, a location and a user identifier.

8. The video capture device of claim 7, wherein the user identifier comprises at least one of a physician identifier or a patient identifier.

9. The video capture device of claim 5, wherein:
the endoscopy device is selected from the group consisting of arthroscopes, cystoscopes, hysteroscopes, laparoscopes, laryngoscopes, endoscopes, resectoscopes, sinuscopes, uteroscopes and colonoscopes.

10. The video capture device of claim 1, wherein the processor is further capable to prepare the recorded video data by applying one or more of compression processing or encryption processing.

11. The video capture device of claim 1, further comprising at least one audio input port.

12. The video capture device of claim 1, wherein the output device comprises at least one of a physical output port or a wireless transmitter.

13. A method for automatically recording a video output signal from an endoscopy device during a recording session, comprising the steps of:
receiving video image data of the video output signal at a video capture device;
transmitting signals corresponding to the video image data and associated metadata to the server via the video capture device;
analyzing the video image data by the video capture device to identify a recording start indicator for the recording session as a function of predetermined threshold conditions, wherein the predetermined threshold conditions are based on two or more elements selected from the group consisting of pixel values, frame-to-frame motion metrics, edge detection indicators audio signals, neural networks, convolutional neural networks, and recurrent neural networks;
setting a recording start timestamp by the video capture device;
transmitting the recording start timestamp data over the network to the server via the video capture device;
indexing the recorded video data by the server as a function of the associated metadata;
storing the indexed video data for the recording session in a database accessible to the server; and storing the recording start timestamp for the recording session in the database, wherein the analyzing step identifies the recording start indicator to initiate the recording session only when the threshold conditions indicate that the medical device is displaying video image data internal to a patient.

14. The method of claim 13, further comprising the steps of:

receiving audio data from at least one microphone; and transmitting signals corresponding to the audio data, associated metadata and an associated timestamp to the server via the video capture device.

15. The method of claim 13, wherein the step of transmitting signals corresponding to the video image data and associated metadata begins substantially coincidently with the step of transmitting recording start timestamp data.

16. The method of claim 13, wherein the step of transmitting signals corresponding to the video image data and associated metadata occurs continuously.

17. The method of claim 13, wherein the endoscopy device is selected from the group consisting of arthroscopes, cystoscopes, hysteroscopes, laparoscopes, laryngoscopes, endoscopes, resectoscopes, sinuscopes, uteroscopes and colonoscopes.

18. The method of claim 13, further comprising the steps of:

analyzing the video image data by the video capture device to identify a recording stop indicator as a function of the predetermined threshold conditions;

setting a recording stop timestamp for the recording session by the video capture device;

transmitting recording stop timestamp data to the server over the network via an output port of the video capture device; and storing the recording start timestamp by the server in the database, wherein the recording stop indicator terminates the recording session when the threshold conditions indicate that the medical device is displaying video image data external to the patient.

19. The method of claim 18, wherein the step of transmitting signals corresponding to the video image data and associated metadata terminates coincidently with the step of transmitting recording stop timestamp data.

20. The method of claim 13, wherein the associated metadata includes data indicating one or more elements selected from the group consisting of a calendar date, a timestamp, a location, and a user identifier.

21. The method of claim 20, wherein the user identifier comprises at least one of a physician identifier or a patient identifier.

22. The method of claim 18, wherein the analyzing steps determine that the medical device is either displaying video image data internal to a patient or external to the patient, as a function of the predetermined threshold conditions.

23. The method of claim 13, further comprising the steps of:

providing a network-accessible user portal by the server;

receiving one of a recording start indicator or a recording stop indicator for the recording session via the network-accessible user portal;

preparing a timestamp for the indicator received by the server; and storing the timestamp for the server in the database.

24. The method of claim 23, wherein the recording start indicator or recording stop indicator is received by the server via a user interface of the portal by means of at least one of a keyboard device, a mouse, a foot pedal or a voice-activated device.

25. The method of claim 24, wherein a recording start indicator is received by the server, further comprising the step of:

applying a contention resolution rule to select only one of the recording start timestamp received from the video capture device or the recording start timestamp for the server, as the recording start timestamp for the recording session.

26. The video capture device of claim 1, wherein the predetermined threshold conditions comprise RGB pixel values.

27. The video capture device of claim 1, wherein the predetermined threshold conditions are based on at least one analysis element selected from the group consisting of pixel values, frame-to-frame motion metrics, edge detection indicators, and audio signals, and at least one neural network element selected from the group consisting of neural networks, convolutional neural networks, and recurrent neural networks, and wherein the threshold conditions based on the at least one analysis element are adjusted by the at least one neural network element.

28. The method of claim 13, wherein the predetermined threshold conditions comprise RGB pixel values.

29. The method of claim 13, wherein the predetermined threshold conditions are based on at least one analysis element selected from the group consisting of pixel values, frame-to-frame motion metrics, edge detection indicators, and audio signals, and at least one neural network element selected from the group consisting of neural networks, convolutional neural networks, and recurrent neural networks, further comprising the step of adjusting the threshold conditions based on the at least one analysis element by the at least one neural network element.

* * * * *